(12) United States Patent
Bokka Srinivasa Rao et al.

(10) Patent No.: US 11,771,352 B2
(45) Date of Patent: Oct. 3, 2023

(54) DEVICE FOR THE ATTACHED FLOW OF BLOOD

(71) Applicant: Becton, Dickinson and Company, Franklin Lakes, NJ (US)

(72) Inventors: Kishore K. Bokka Srinivasa Rao, Ridgewood, NJ (US); Jayeon Kim, River Edge, NJ (US); Milan Ivosevic, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 188 days.

(21) Appl. No.: 16/327,137

(22) PCT Filed: Aug. 23, 2017

(86) PCT No.: PCT/US2017/048147
§ 371 (c)(1),
(2) Date: Feb. 21, 2019

(87) PCT Pub. No.: WO2018/039307
PCT Pub. Date: Mar. 1, 2018

(65) Prior Publication Data
US 2019/0223772 A1    Jul. 25, 2019

Related U.S. Application Data

(60) Provisional application No. 62/378,971, filed on Aug. 24, 2016.

(51) Int. Cl.
*A61B 5/15* (2006.01)

(52) U.S. Cl.
CPC .. *A61B 5/150389* (2013.01); *A61B 5/150022* (2013.01); *A61B 5/15045* (2013.01); *A61B 5/150068* (2013.01); *A61B 5/150106* (2013.01); *A61B 5/150251* (2013.01); *A61B 5/150259* (2013.01); *A61B 5/150343* (2013.01); *A61B 5/150404* (2013.01); *A61B 5/150755* (2013.01)

(58) Field of Classification Search
CPC ........ A61B 5/150022; A61B 5/150068; A61B 5/150106; A61B 5/150251; A61B 5/150259; A61B 5/150267; A61B 5/150343; A61B 5/150389; A61B 5/150396; A61B 5/150404; A61B 5/15045; A61B 5/150458; A61B 5/150748; A61B 5/150755; A61B 5/15105; A61B 5/15142; A61B 5/150206
See application file for complete search history.

(56) References Cited

U.S. PATENT DOCUMENTS

| 2,646,799 A | 7/1953 | Jacoby, Jr. |
| 3,623,475 A | 11/1971 | Sanz et al. |

(Continued)

FOREIGN PATENT DOCUMENTS

| DE | 10315396 A1 | 10/2004 |
| EP | 0224650 A2 | 6/1987 |

(Continued)

*Primary Examiner* — Patrick Fernandes
(74) *Attorney, Agent, or Firm* — The Webb Law Firm

(57) ABSTRACT

A collection device (10) which directs a flow of blood into a container (14) and provides a controlled blood flow path that ensures blood flow from a collection site to a collection container is disclosed.

18 Claims, 13 Drawing Sheets

(56) References Cited

U.S. PATENT DOCUMENTS

| | | |
|---|---|---|
| 3,626,929 A | 12/1971 | Sanz et al. |
| 3,630,191 A | 12/1971 | Gilford |
| 3,741,197 A | 6/1973 | Sanz et al. |
| 4,024,857 A | 5/1977 | Blecher et al. |
| 4,397,318 A | 8/1983 | Burns |
| 4,411,163 A | 10/1983 | White |
| 4,620,549 A | 11/1986 | Nugent |
| 4,646,753 A | 3/1987 | Nugent |
| 4,690,153 A | 9/1987 | Losada et al. |
| 4,805,635 A | 2/1989 | Korf et al. |
| 5,014,718 A | 5/1991 | Mitchen |
| 5,038,794 A | 8/1991 | Van Valkenburg |
| 5,070,886 A | 12/1991 | Mitchen et al. |
| 5,181,523 A | 1/1993 | Wendelborn |
| 5,384,096 A | 1/1995 | Burns |
| 5,458,854 A | 10/1995 | Burns |
| 5,485,856 A | 1/1996 | Buckland |
| 5,569,223 A | 10/1996 | Wandell et al. |
| 5,624,458 A | 4/1997 | Lipscher |
| 5,662,127 A | 9/1997 | De Vaughn |
| 5,709,699 A | 1/1998 | Warner |
| 5,843,112 A | 12/1998 | De Vaughn |
| 5,857,983 A | 1/1999 | Douglas et al. |
| 5,891,053 A | 4/1999 | Sesekura |
| 5,951,492 A | 9/1999 | Douglas et al. |
| 5,951,493 A | 9/1999 | Douglas et al. |
| 6,048,352 A | 4/2000 | Douglas et al. |
| 6,071,250 A | 6/2000 | Douglas et al. |
| 6,319,210 B1 | 11/2001 | Douglas et al. |
| 6,352,514 B1 | 3/2002 | Douglas et al. |
| 6,485,439 B1 | 11/2002 | Roe et al. |
| 6,503,210 B1 | 1/2003 | Hirao et al. |
| 6,551,267 B1 | 4/2003 | Cohen et al. |
| 6,589,260 B1 | 7/2003 | Schmelzeisen-Redeker et al. |
| 6,626,851 B2 | 9/2003 | Hirao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| D488,232 S | 4/2004 | Nan |
| D488,588 S | 4/2004 | Murphy |
| 7,131,984 B2 | 11/2006 | Sato et al. |
| 7,201,723 B2 | 4/2007 | Chan |
| 7,291,159 B2 | 11/2007 | Schmelzeisen-Redeker et al. |
| D569,514 S | 5/2008 | Poll et al. |
| 7,384,402 B2 | 6/2008 | Wong et al. |
| D576,277 S | 9/2008 | Oren et al. |
| D582,037 S | 12/2008 | Poll et al. |
| 7,591,791 B2 | 9/2009 | Keren |
| 7,727,168 B2 | 6/2010 | Douglas et al. |
| 7,731,668 B2 | 6/2010 | Douglas et al. |
| 7,758,516 B2 | 7/2010 | Perez |
| 7,758,518 B2 | 7/2010 | Perez et al. |
| 7,758,602 B2 | 7/2010 | Sato et al. |
| 7,841,991 B2 | 11/2010 | Douglas et al. |
| 8,062,274 B2 | 11/2011 | Rasch-Menges et al. |
| 8,360,993 B2 | 1/2013 | Escutia et al. |
| 8,372,015 B2 | 2/2013 | Escutia et al. |
| 8,376,959 B2 | 2/2013 | Deck |
| 8,475,395 B2 | 7/2013 | Nakayama et al. |
| 8,523,894 B2 | 9/2013 | Schmelzeisen-Redeker et al. |
| 8,636,674 B2 | 1/2014 | Roe |
| 8,684,949 B2 | 4/2014 | Hoenes et al. |
| 8,690,798 B2 | 4/2014 | Douglas et al. |
| D707,364 S | 6/2014 | Spencer |
| 8,740,813 B2 | 6/2014 | Douglas et al. |
| 8,858,467 B2 | 10/2014 | List et al. |
| 8,926,644 B2 | 1/2015 | Schiff et al. |
| 8,956,307 B2 | 2/2015 | Morita et al. |
| D732,684 S | 6/2015 | Ooi et al. |
| D742,005 S | 10/2015 | Komuda et al. |
| 9,226,704 B2 | 1/2016 | Deck |
| 9,289,763 B2 | 3/2016 | Berthier et al. |
| 9,295,416 B2 | 3/2016 | Bartfeld et al. |
| D757,267 S | 5/2016 | Shi |
| 9,326,718 B2 | 5/2016 | Petrich et al. |
| 9,332,931 B2 | 5/2016 | Chan |
| 9,380,963 B2 | 7/2016 | Gofman et al. |
| 9,380,970 B2 | 7/2016 | Christensen et al. |
| 9,380,975 B2 | 7/2016 | Karbowniczek et al. |
| 9,414,774 B2 | 8/2016 | Korner et al. |
| 9,427,184 B2 | 8/2016 | Holmes et al. |
| 9,456,782 B2 | 10/2016 | Rasch-Menges et al. |
| 9,538,941 B2 | 1/2017 | Perez et al. |
| 9,554,741 B2 | 1/2017 | Roe et al. |
| 9,556,027 B2 | 1/2017 | Chakravarti et al. |
| 9,566,027 B2 | 2/2017 | Tamir |
| 9,636,051 B2 | 5/2017 | Emery et al. |
| 9,681,834 B2 | 6/2017 | Suess |
| D800,333 S | 10/2017 | Snider et al. |
| 9,833,183 B2 | 12/2017 | Escutia et al. |
| 9,849,251 B2 | 12/2017 | Crawford et al. |
| 10,093,918 B2 | 10/2018 | Mielke et al. |
| 10,126,211 B2 | 11/2018 | Yamakawa et al. |
| 10,136,848 B2 | 11/2018 | Hsiung et al. |
| 10,251,589 B2 | 4/2019 | Korner et al. |
| D856,148 S | 8/2019 | Lucas, Jr. et al. |
| D868,269 S | 11/2019 | Sayre |
| 10,499,840 B2 | 12/2019 | Bartfeld et al. |
| D881,410 S | 4/2020 | Motadel et al. |
| D882,113 S | 4/2020 | Motadel et al. |
| 10,610,142 B1 | 4/2020 | Diju et al. |
| 10,631,771 B2 | 4/2020 | Naghavi et al. |
| 10,722,163 B2 | 7/2020 | McHale et al. |
| 2003/0195540 A1 | 10/2003 | Moerman |
| 2004/0092843 A1 | 5/2004 | Kreiser et al. |
| 2004/0127818 A1 | 7/2004 | Roe et al. |
| 2005/0215923 A1 | 9/2005 | Wiegel |
| 2005/0234486 A1 | 10/2005 | Allen et al. |
| 2005/0234489 A1 | 10/2005 | Allen |
| 2005/0234491 A1 | 10/2005 | Allen et al. |
| 2005/0277849 A1 | 12/2005 | Wong et al. |
| 2006/0052809 A1 | 3/2006 | Karbowniczek et al. |
| 2007/0060842 A1 | 3/2007 | Alvarez-Icaza et al. |
| 2007/0060843 A1 | 3/2007 | Alvarez-Icaza et al. |
| 2007/0060844 A1 | 3/2007 | Alvarez-Icaza et al. |
| 2007/0073187 A1 | 3/2007 | Thomson et al. |
| 2007/0073191 A1 | 3/2007 | Thomson et al. |
| 2007/0083130 A1 | 4/2007 | Thomson et al. |
| 2007/0083131 A1 | 4/2007 | Escutia et al. |
| 2007/0093863 A1 | 4/2007 | Pugh |
| 2007/0093864 A1 | 4/2007 | Pugh |
| 2007/0112281 A1 | 5/2007 | Olson |
| 2007/0112367 A1 | 5/2007 | Olson |
| 2007/0156065 A1 | 7/2007 | Chan |
| 2008/0294064 A1 | 11/2008 | Calasso et al. |
| 2009/0112121 A1 | 4/2009 | Chuang et al. |
| 2009/0112122 A1 | 4/2009 | Chuang et al. |
| 2009/0112125 A1 | 4/2009 | Tamir |
| 2009/0177224 A1 | 7/2009 | Naghavi et al. |
| 2009/0198152 A1 | 8/2009 | Kim |
| 2009/0259145 A1 | 10/2009 | Bartfeld et al. |
| 2009/0287117 A1 | 11/2009 | Harttig et al. |
| 2010/0010374 A1 | 1/2010 | Escutia et al. |
| 2010/0036281 A1 | 2/2010 | Doi |
| 2010/0113981 A1 | 5/2010 | Oki et al. |
| 2010/0261988 A1 | 10/2010 | Tamir |
| 2011/0092854 A1 | 4/2011 | Kraemer et al. |
| 2011/0118568 A1 | 5/2011 | Sei |
| 2011/0124984 A1* | 5/2011 | Rostaing ............ A61B 5/14514 422/513 |
| 2011/0270129 A1 | 11/2011 | Hoerauf |
| 2013/0211289 A1 | 8/2013 | Moga et al. |
| 2014/0318282 A1 | 10/2014 | Blekher et al. |
| 2015/0105813 A1 | 4/2015 | Li et al. |
| 2015/0351676 A1 | 12/2015 | Faurie et al. |
| 2016/0174888 A1* | 6/2016 | Berthier ............ A61B 5/150412 600/575 |
| 2016/0302708 A1 | 10/2016 | Christensen et al. |
| 2016/0367176 A1 | 12/2016 | Korner et al. |
| 2017/0020426 A1 | 1/2017 | Holmes et al. |
| 2017/0079569 A1 | 3/2017 | Rasch-Menges et al. |
| 2017/0122846 A1 | 5/2017 | Holmes et al. |
| 2017/0181682 A1 | 6/2017 | Tamir |
| 2018/0214059 A1 | 8/2018 | Escutia et al. |

(56) References Cited

U.S. PATENT DOCUMENTS

| | | |
|---|---|---|
| 2018/0220944 A1 | 8/2018 | Otsubo et al. |
| 2018/0303385 A1 | 10/2018 | Hatamian et al. |
| 2018/0306831 A1 | 10/2018 | Hatamian |
| 2019/0015030 A1 | 1/2019 | Barker |
| 2019/0099117 A1 | 4/2019 | Pulitzer et al. |
| 2019/0184100 A1 | 6/2019 | Fukuda et al. |
| 2019/0212345 A1 | 7/2019 | Lam et al. |
| 2019/0261961 A1 | 8/2019 | Esfandiari |
| 2019/0371136 A1 | 12/2019 | Whitaker |
| 2020/0054260 A1 | 2/2020 | Hatamian |
| 2021/0030346 A1 | 2/2021 | Noguchi et al. |

FOREIGN PATENT DOCUMENTS

| | | |
|---|---|---|
| EP | 0224650 B1 | 6/1992 |
| EP | 1157660 A1 | 11/2001 |
| EP | 1157660 B1 | 9/2007 |
| EP | 2184012 A1 | 5/2010 |
| EP | 2243427 B1 | 4/2013 |
| EP | 2184012 B1 | 6/2013 |
| GB | 2183159 A | 6/1987 |
| GB | 2409411 A | 6/2005 |
| JP | S61284235 A | 12/1986 |
| JP | H04506024 A | 10/1992 |
| JP | 2002219115 A | 8/2002 |
| JP | 200594425 A | 4/2005 |
| JP | 2005131009 A | 5/2005 |
| JP | 2006043016 A | 2/2006 |
| JP | 2007111215 A | 5/2007 |
| JP | 200899991 A | 5/2008 |
| JP | 2009542304 A | 12/2009 |
| JP | 2011078518 A | 4/2011 |
| JP | 2011513754 A | 4/2011 |
| JP | 4762341 B2 | 8/2011 |
| JP | 2011522593 A | 8/2011 |
| RU | 2580295 C2 | 7/2015 |
| WO | 02100254 A2 | 12/2002 |
| WO | 2004064637 A1 | 8/2004 |
| WO | 2008027319 A2 | 3/2008 |
| WO | 2009081405 A2 | 7/2009 |
| WO | 2009095184 A1 | 8/2009 |
| WO | 2009145920 A1 | 12/2009 |
| WO | 2014063344 A1 | 5/2014 |
| WO | 2015191853 A1 | 12/2015 |
| WO | 2016161083 A1 | 10/2016 |
| WO | 2017221698 A1 | 12/2017 |
| WO | 2018160523 A1 | 9/2018 |
| WO | 2018218341 A1 | 12/2018 |
| WO | 2019220938 A1 | 11/2019 |
| WO | 2020047070 A1 | 3/2020 |

* cited by examiner

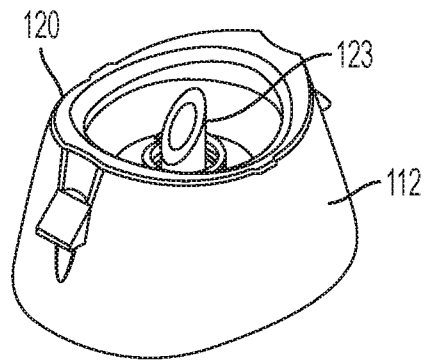
FIG. 18
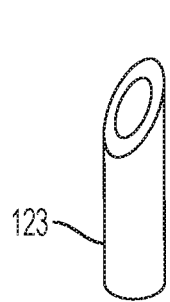    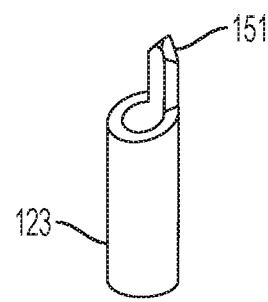    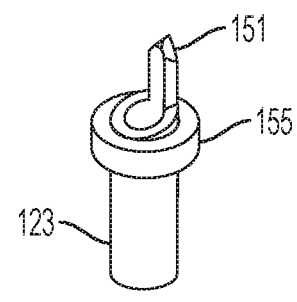
FIG. 19    FIG. 20    FIG. 21
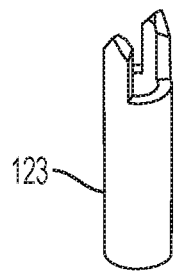    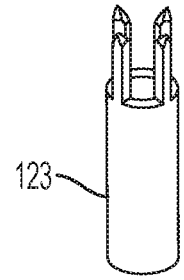    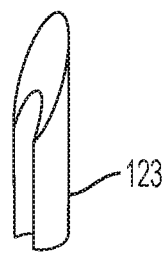
FIG. 22    FIG. 23    FIG. 24

DEVICE FOR THE ATTACHED FLOW OF BLOOD

CROSS-REFERENCE TO RELATED APPLICATIONS

The present application is the United States national phase of International Application No. PCT/US2017/048147 filed Aug. 23, 2017, and claims priority to U.S. Provisional Application No. 62/378,971, filed Aug. 24, 2016, entitled "Finger-Based Capillary Blood Collection Device", the entire disclosures of which are hereby incorporated by reference.

BACKGROUND OF THE INVENTION

1. Field of the Disclosure

The present disclosure relates generally to devices adapted for use with biological fluids. More particularly, the present disclosure relates to devices for controlling the flow of blood.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including chemical composition, hematology, or coagulation, for example. Blood tests determine the physiological and biochemical states of the patient, such as disease, mineral content, drug effectiveness, and organ function. Blood tests may be performed in a clinical laboratory or at the point-of-care near the patient.

Lancet devices are used in the medical field for puncturing the skin of a patient to obtain a small sample of capillary blood from the patient. Certain diseases, such as diabetes, require that a patient's blood be tested on a regular basis to monitor, for example, the patient's blood sugar levels. Additionally, test kits, such as cholesterol test kits, often require a small blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Upon puncturing the skin of a patient using a lancet device, the blood will spread and remain on a surface of the finger.

SUMMARY OF THE INVENTION

The present disclosure provides a collection device which directs a flow of blood into a container and provides a controlled blood flow path that ensures blood flow from a collection site to a collection container.

The device for attached flow of blood of the present disclosure achieves this using three key technical elements to control the flow of blood in the desired manner. First, controlling and guiding a blood sample from a skin surface of a patient to a collection housing via a first flow directing attachment portion. Second, controlling and guiding the blood sample from a first end of a collection housing to a second end of the collection housing via capillary transfer. Third, controlling and guiding the blood sample from the second end of the collection housing into a collection cavity of a collection container via a second flow directing attachment portion. With a first end of a housing in communication with a source of blood, a first flow directing attachment portion, a flow channel, a second flow directing attachment portion, and an interior wall surface of a container provide attachment portions to establish attached blood flow, for a first drop of blood and subsequent blood to follow, from the first end of the housing to a collection cavity of the container.

In accordance with an embodiment of the present invention, a device for attached flow of blood includes a housing defining a centerline and having a first end, a second end, and a flow channel having an inlet and an outlet, a portion of the flow channel offset from the centerline of the housing, and the flow channel having a first flow directing attachment portion adjacent the inlet and a second flow directing attachment portion adjacent the outlet; and a container removably connectable to the housing, the container defining a collection cavity and having an interior wall, wherein, with the container connected to the housing, the outlet of the flow channel is in fluid communication with the collection cavity of the container and the outlet of the flow channel is adjacent the interior wall of the container.

In one configuration, the first flow directing attachment portion provides a first fluid attachment point for blood to attach to for controlling the flow of blood from a skin surface to a portion of the housing. In another configuration, the second flow directing attachment portion provides a second fluid attachment point for blood to attach to for controlling the flow of blood from a portion of the housing to the collection cavity of the container. In yet another configuration, with the first end of the housing in communication with a source of blood, the first flow directing attachment portion, the flow channel, the second flow directing attachment portion, and the interior wall of the container provide attachment portions to establish attached blood flow, for a first drop of blood and subsequent blood to follow, from the first end of the housing to the collection cavity of the container. In one configuration, with the inlet of the flow channel in communication with a source of blood, the blood fluidly attaches to the first flow directing attachment portion and flows from the first flow directing attachment portion to the flow channel. In another configuration, the blood is subsequently pulled through the flow channel to the second flow directing attachment portion via capillary action. In yet another configuration, the blood fluidly attaches to the second flow directing attachment portion and the interior wall of the container to flow from the flow channel into the collection cavity of the container. In one configuration, the first end of the housing includes a sloped wall surface, the first flow directing attachment portion extends from the sloped wall surface, and the sloped wall surface defines a flow channel entry. In another configuration, the first flow directing attachment portion is an attachment pillar. In yet another configuration, the first flow directing attachment portion comprises a plurality of attachment pillars. In one configuration, the second flow directing attachment portion is an attachment lip. In another configuration, the second flow directing attachment portion is an extended capillary tube portion. In yet another configuration, the second flow directing attachment portion is an inward curved lip. In one configuration, the second flow directing attachment portion is a planar cut lip. In another configuration, the second flow directing attachment portion is an extended pillar structure.

In yet another configuration, the outlet of the flow channel extends beyond the second end of the housing.

In accordance with another embodiment of the present invention, a device for attached flow of blood includes a housing defining a centerline and having a first end, a second end, a hollow needle, and a flow channel having an inlet and an outlet, a portion of the flow channel offset from the centerline of the housing, the flow channel having a flow directing attachment portion adjacent the outlet, and the hollow needle between the first end of the housing and the flow channel; and a container removably connectable to the housing, the container defining a collection cavity and having an interior wall, wherein, with the container connected to the housing, the outlet of the flow channel is in fluid communication with the collection cavity of the container and the outlet of the flow channel is adjacent the interior wall of the container.

In one configuration, the flow directing attachment portion provides a fluid attachment point for blood to attach to for controlling the flow of blood from a portion of the housing to the collection cavity of the container. In another configuration, with the first end of the housing in communication with a source of blood, the hollow needle, the flow channel, the flow directing attachment portion, and the interior wall of the container provide attachment portions to establish attached blood flow, for a first drop of blood and subsequent blood to follow, from the first end of the housing to the collection cavity of the container. In yet another configuration, with the inlet of the flow channel in communication with a source of blood, the blood fluidly attaches to a portion of the hollow needle and flows through the hollow needle to the flow channel. In one configuration, the blood is subsequently pulled through the flow channel to the flow directing attachment portion via capillary action. In another configuration, the blood fluidly attaches to the flow directing attachment portion and the interior wall of the container to flow from the flow channel into the collection cavity of the container. In yet another configuration, the housing includes a sloped wall surface between the hollow needle and the flow channel, and the sloped wall surface defines a flow channel entry. In one configuration, the flow directing attachment portion is an attachment lip. In another configuration, the flow directing attachment portion is an extended capillary tube portion. In yet another configuration, the flow directing attachment portion is an inward curved lip. In one configuration, the flow directing attachment portion is a planar cut lip. In another configuration, the flow directing attachment portion is an extended pillar structure. In yet another configuration, the outlet of the flow channel extends beyond the second end of the housing. In one configuration, the device further includes a flow directing ring around the hollow needle. In another configuration, the hollow needle includes a lancing blade. In yet another configuration, with the first end of the housing in communication with a source of blood, a first drop of blood attaches to the lancing blade and flows through the hollow needle to the flow channel.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 18 is a perspective view of a hollow needle of a device for attached flow of blood in accordance with an embodiment of the present invention.

FIG. 19 is a perspective view of a hollow needle of a device for attached flow of blood in accordance with another embodiment of the present invention.

FIG. 20 is a perspective view of a hollow needle of a device for attached flow of blood in accordance with another embodiment of the present invention.

FIG. 21 is a perspective view of a hollow needle of a device for attached flow of blood in accordance with another embodiment of the present invention.

FIG. 22 is a perspective view of a hollow needle of a device for attached flow of blood in accordance with another embodiment of the present invention.

FIG. 23 is a perspective view of a hollow needle of a device for attached flow of blood in accordance with another embodiment of the present invention.

FIG. 24 is a perspective view of a hollow needle of a device for attached flow of blood in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
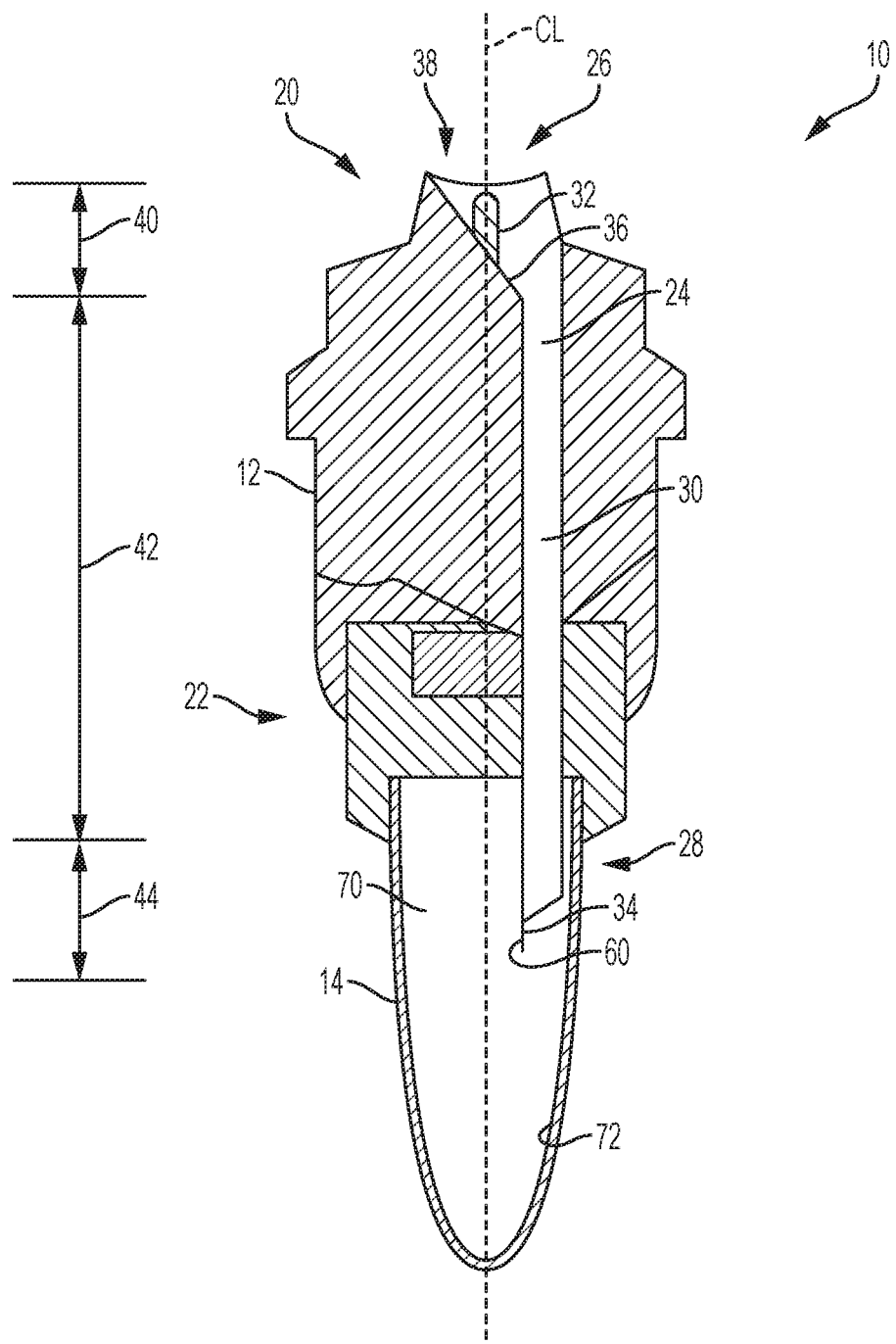
FIG. 1 is a cross-sectional view of a device for attached flow of blood in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The device for attached flow of blood 10 of the present disclosure provides a controlled blood flow path that ensures attached blood flow from a collection site to a collection container. The device for attached flow of blood 10 of the present disclosure achieves this using three key technical elements to control the flow of blood in the desired manner. First, controlling and guiding a blood sample from a skin surface of a patient to a collection housing via a first flow directing attachment portion. Second, controlling and guiding the blood sample from a first end of a collection housing to a second end of the collection housing via capillary transfer. Third, controlling and guiding the blood sample from the second end of the collection housing into a collection cavity of a collection container via a second flow directing attachment portion.

FIGS. 1-10B illustrate an exemplary embodiment of a device for attached flow of blood of the present disclosure. Referring to FIGS. 1-10B, a device for attached flow of blood 10 of the present disclosure provides a controlled blood flow path that ensures attached blood flow from a collection site to a collection container.

Upon puncturing the skin of a patient using a typical lancet device, the blood will spread and remain on a surface of the finger. Without controlling the blood and the flow of blood, the blood may remain on a surface of the finger and may not readily flow to a collection container.

Referring to FIGS. 1-10B, in one exemplary embodiment, a device for attached flow, i.e., providing flow directing attachment portions for a blood sample to attach to for guiding and controlling the flow of the blood sample from a collection site to a collection container, of blood 10 generally includes a housing 12 and a collection container 14 that is removably connectable to the housing 12. The container 14 defines a collection cavity 70 and includes an interior wall or interior wall surface 72.

Figure 2:
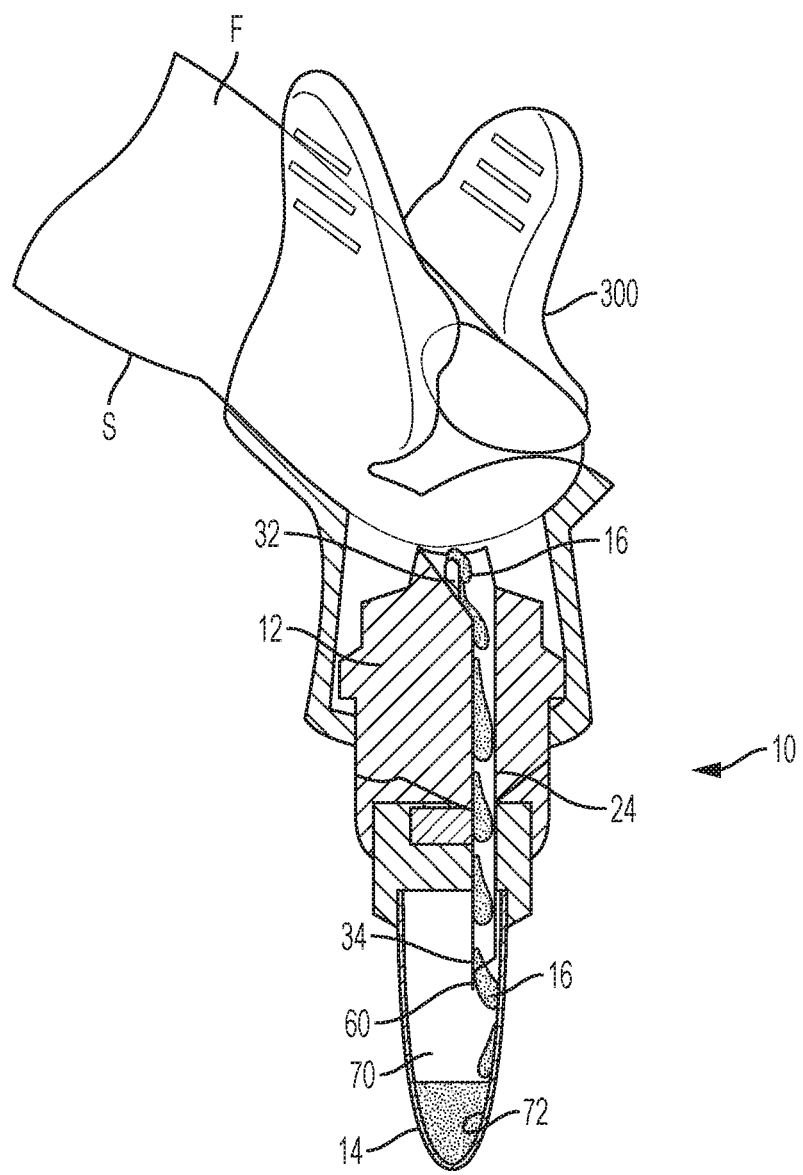
FIG. 2 is the device of FIG. 1 engaged with a finger in accordance with an embodiment of the present invention.
Figure 3:
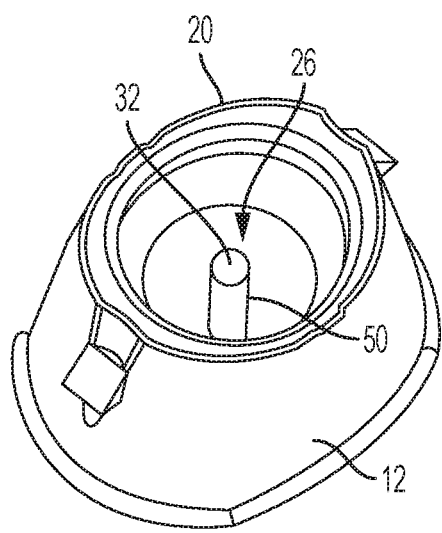
FIG. 3 is a perspective view of a first flow directing attachment portion of a device for attached flow of blood in accordance with an embodiment of the present invention.

Referring to FIGS. 1-10B, the housing 12 defines a centerline CL and includes a first end 20, a second end 22, and a flow channel 24. The flow channel 24 includes an inlet 26 and an outlet 28. A portion of the flow channel 24, e.g., a middle portion 30, is offset from the centerline CI of the housing 12. This ensures that the outlet 28 of the flow channel 24 is adjacent to an interior wall surface 72 of the container 14, as described in more detail below. The flow channel 24 also includes a first flow directing attachment portion 32 at the inlet 26 and a second flow directing attachment portion 34 at the outlet 28. In one embodiment, the outlet 28 of the flow channel 24 extends beyond the second end 22 of the housing 12 as shown in FIGS. 1 and 2.

Referring to FIGS. 1 and 2, with the container 14 connected to the housing 12, the outlet 28 of the flow channel 24 is in fluid communication with the collection cavity 70 of the container 14 and the outlet 28 of the flow channel 24 is adjacent the interior wall surface 72 of the container 14.

In one embodiment, the first end 20 of the housing 12 includes a sloped wall surface 36. In this manner, the sloped wall surface 36 provides physical structure, i.e., a wall surface, which allows the first flow directing attachment portion 32 to extend upwards from. For example, referring to FIG. 1, the first flow directing attachment portion 32 extends upwards from the sloped wall surface 36 to the inlet 26 of the housing 12. In one embodiment, the sloped wall surface 38 defines a flow channel entry 38.

The device for attached flow of blood 10 of the present disclosure provides a controlled blood flow path that ensures attached blood flow from a collection site to a collection container. The device for attached flow of blood 10 of the present disclosure achieves this using three key technical elements to control the flow of blood in the desired manner. First, controlling and guiding a blood sample from a skin surface of a patient to a collection housing via a first flow directing attachment portion. Second, controlling and guiding the blood sample from a first end of a collection housing to a second end of the collection housing via capillary transfer. Third, controlling and guiding the blood sample from the second end of the collection housing into a collection cavity of a collection container via a second flow directing attachment portion.

For example, referring to FIG. 2, with the first end 20 of the housing 12 in communication with a source of blood 16, the first flow directing attachment portion 32, the flow channel 24, the second flow directing attachment portion 34, and the interior wall surface 72 of the container 14 provide attachment portions to establish attached blood flow, for a first drop of blood 16 and subsequent blood 16 to follow, from the first end 20 of the housing 12 to a collection cavity 70 of the container 14.

The first key blood flow path element 40 involves directing the first drop of blood 16 away from a surface S of a finger F in a direction towards a collection container 14. In one embodiment, with the first end 20 of the housing 12 in communication with a source of blood 16, the first flow directing attachment portion 32 provides a pillar which the first drop of blood 16 attaches to and flows down and into the flow channel 24 of the housing 12 in a controlled manner. In other words, a first drop of blood 16 attaches to the first flow directing attachment portion 32 and flows from the first flow directing attachment portion 32 to the flow channel 24.

In one embodiment, the sloped wall surface 36 provides a downward attached flow path from the first flow directing attachment portion 32 to the flow channel 24 of the housing 12. After the first drop of blood 16 attaches to and flows down the first flow directing attachment portion 32, the subsequent blood 16 follows the attached blood flow path of the first drop of blood 16 from the first end 20 of the housing 12 to the collection cavity 70 of the container 14.

The second key blood flow path element 42 involves directing the blood 16 down the flow channel 24 to the second flow directing attachment portion 34 in a direction towards a collection container 14. For example, the first drop of blood 16, and subsequent blood 16, is pulled through the flow channel 24 to the second flow directing attachment portion 34 via capillary motion. In one embodiment, the flow channel 24 is a capillary flow channel. In one embodiment, the flow channel 24 is a capillary tube that uses capillary forces to pull the blood 16 down the flow channel 24 away from the surface S of the finger F.

The third key blood flow path element 44 involves directing the blood 16 from the flow channel 24 into the collection container 14. The device 10 of the present disclosure ensures transition from the flow channel 24 to the container 14 via attached flow. For example, the blood 16 attaches to the second flow directing attachment portion 34 and the interior wall surface 72 of the container 14 to flow from the flow channel 24 into the collection cavity 70 of the container 14.

The third key blood flow path element 44 involving directing the blood 16 from the flow channel 24 into the collection container 14 is the reason that it is important that a portion of the flow channel 24, e.g., a middle portion 30, is offset from the centerline CL of the housing 12. This ensures that the outlet 28 of the flow channel 24, and the second flow directing attachment portion 34, is adjacent to an interior wall surface 72 of the container 14 to ensure the transition of the attached blood flow from the flow channel 24 to the container 14.

The blood 16 will only flow down and out the flow channel 24 into the container 14 if the blood 16 is able to find another portion to attach to. The second flow directing attachment portion 34 and the interior wall surface 72 of the container 14 provide such attachment portions to control the blood 16 to the collection cavity 70 of the container 14 via attached blood flow.

As described above, once this pathway of attached blood flow is established, the subsequent blood 16 follows and flows along this attached blood flow. In the above-described manner, the device 10 of the present disclosure establishes attached blood flow, for a first drop of blood 16 and subsequent blood 16 to follow, from the first end 20 of the housing 12 to a collection cavity 70 of the container 14.

The first flow directing attachment portion 32 may include a variety of different designs and structures as shown in FIGS. 3-6. Additional alternative designs and structures of the first flow directing attachment portion 32 are contemplated. For example, referring to FIG. 3, in one embodiment, the first flow directing attachment portion 32 is an attachment pillar 50. The attachment pillar 50 is a single pillar structure that may have a variable diameter and length. The pillar 50 may include hydrophilic surface properties to attract the first drop of blood and establish a flow path to the second capillary section. In one embodiment, the pillar 50 may have a diameter of between 0.25 mm to 4 mm, and a length of between 2 mm and 20 mm.

Figure 4:
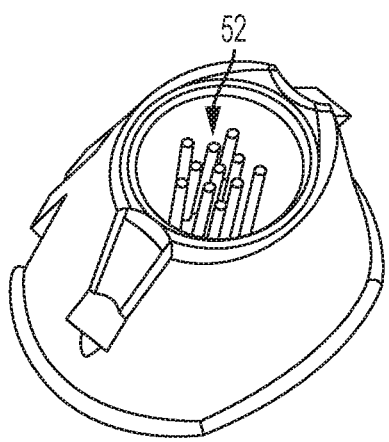
FIG. 4 is a perspective view of a first flow directing attachment portion of a device for attached flow of blood in accordance with another embodiment of the present invention.

Referring to FIG. 4, in another embodiment, the first flow directing attachment portion 32 is a plurality of attachment pillars 52. The plurality of attachment pillars 52 may include pillars having different sizes and structures including a variety of different number of pillars. In one configuration, the plurality of attachment pillars 52 provide multiple surfaces for the first drop of blood to establish a flow path without smearing to the side of the structure or pooling in an undesired location. The multiple pillars 52 can also provide for additional capillary action due to the multiple capillary sections created between the individual pillar structures. In one configuration, the plurality of attachment pillars 52 may include between 2 and 10 attachment pillars, such as between 5 and 10 attachment pillars. In one embodiment, the each pillar may have a diameter of between 0.25 mm to 4 mm, and a length of between 2 mm and 20 mm.

Figure 5:
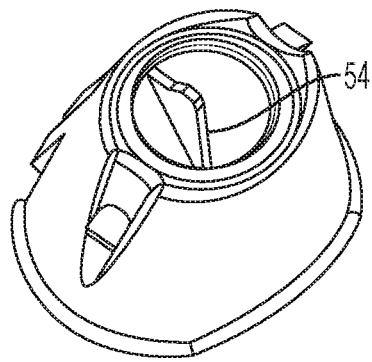
FIG. 5 is a perspective view of a first flow directing attachment portion of a device for attached flow of blood in accordance with another embodiment of the present invention.

Referring to FIG. 5, in another embodiment, the first flow directing attachment portion 32 is a protruding structure 54. The protruding structure 54 guides the attached flow of blood and may include different shapes, sizes, and structures. In this configuration, the slanted structure provides a hydrophilic surface for the first drop of blood to attach to and be guided to the second capillary section. Optionally the thickness of the slanted structure may be from about 0.25 to about 5 mm.

Figure 6:
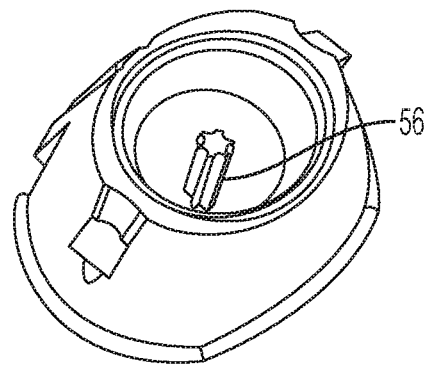
FIG. 6 is a perspective view of a first flow directing attachment portion of a device for attached flow of blood in accordance with another embodiment of the present invention.

Referring to FIG. 6, in another embodiment, the first flow directing attachment portion 32 is a capillary groove portion 56. The capillary groove portion 56 guides the attached flow of blood and may include different shapes, sizes, and number of grooves. In this configuration, the pillar structure having grooves aids with higher capillary force due to the increased surface in the grooves thereby acting as capillary channels for the first drop of blood to be wicked from the finger and transferred to the second capillary channel. In one configuration, the number of grooves provided may be between 1 and 20, and the diameter of each groove may be between 0.25 mm and 1 mm.

The second flow directing attachment portion 34 may include a variety of different designs and structures as shown in FIGS. 7A-10B. Additional alternative designs and structures of the second flow directing attachment portion 34 are contemplated. For example, referring to FIGS. 1 and 2, in one embodiment, the second flow directing attachment portion 34 is an attachment lip 60. The attachment lip 60 is a lip designed to establish attached blood flow into the collection cavity 70 of the container 14 as described above. The attachment lip 60 provides a surface for the blood to expand and form a droplet to establish attachment to the collection cavity.

Figure 7A:
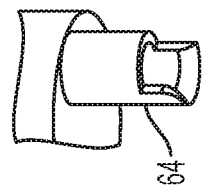
FIG. 7A is a perspective view of a second flow directing attachment portion of a device for attached flow of blood in accordance with an embodiment of the present invention.
Figure 7B:
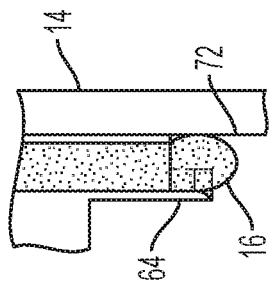
FIG. 7B is a perspective view of the attached flow of blood with a second flow directing attachment portion and an interior wall of a container in accordance with an embodiment of the present invention.

Referring to FIGS. 7A and 7B, in another embodiment, the second flow directing attachment portion 34 is an extended capillary tube portion 62. In one configuration, the extended capillary tube portion may extend between 2 mm and 10 mm beyond the flow channel 24. The extended capillary tube portion 62 may be spaces from the wall of the collection container a distance of less than 1 mm.

Figure 8A:
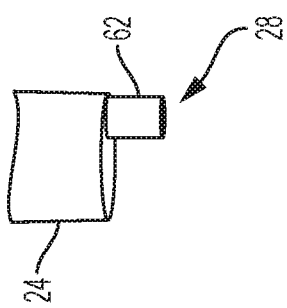
FIG. 8A is a perspective view of a second flow directing attachment portion of a device for attached flow of blood in accordance with another embodiment of the present invention.
Figure 8B:
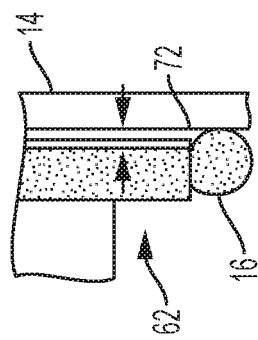
FIG. 8B is a perspective view of the attached flow of blood with a second flow directing attachment portion and an interior wall of a container in accordance with another embodiment of the present invention.

Referring to FIGS. 8A and 8B, in another embodiment, the second flow directing attachment portion 34 is an inward curved lip 64. The inward curved lip structure aids in the attachment of the blood from a portion of the housing to the surface of the collection cavity. In one configuration, the inward curved lip structure may extend beyond the flow channel 24 from about 0.5 to about 10 mm.

Figure 9A:
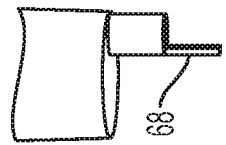
FIG. 9A is a perspective view of a second flow directing attachment portion of a device for attached flow of blood in accordance with another embodiment of the present invention.
Figure 9B:
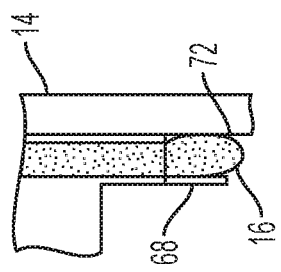
FIG. 9B is a perspective view of the attached flow of blood with a second flow directing attachment portion and an interior wall of a container in accordance with another embodiment of the present invention.

Referring to FIGS. 9A and 9B, in another embodiment, the second flow directing attachment portion 34 is a planar cut lip 66. The planar cut lip 66 also aids in the formation of a blood droplet and the establishment of an attachment of blood to the surface of a collection cavity. In one configuration, the planar cut lip may have an angle from about 10° to about 80°.

Figure 10A:
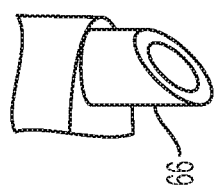
FIG. 10A is a perspective view of a second flow directing attachment portion of a device for attached flow of blood in accordance with another embodiment of the present invention.
Figure 10B:
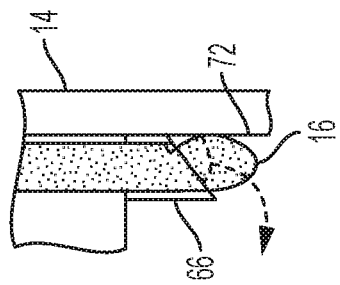
FIG. 10B is a perspective view of the attached flow of blood with a second flow directing attachment portion and an interior wall of a container in accordance with another embodiment of the present invention.

Referring to FIGS. 10A and 10B, in another embodiment, the second flow directing attachment portion 34 is an extended pillar structure 68. In one configuration, the extended pillar structure may extend beyond the flow channel 24 a distance of from about 0.5 mm to about 10 mm.

Referring to FIGS. 1, 2, 17, and 25A-28B, exemplary embodiments of a collection container 14 of the present disclosure are shown. Additional alternative designs and structures of the container 14 are contemplated. A collection container 14 of the present disclosure is removably connectable to the housing 12. The container 14 defines a collection cavity 70 and includes an interior wall or interior wall surface 72. Referring to FIGS. 1 and 2, with the container 14 connected to the housing 12, the outlet 28 of the flow channel 24 is in fluid communication with the collection cavity 70 of the container 14 and the outlet 28 of the flow channel 24 is adjacent the interior wall surface 72 of the container 14. In one configuration, the inner diameter of the flow channel 24 may be from about 0.5 mm to about 2 mm.

Figure 25C:
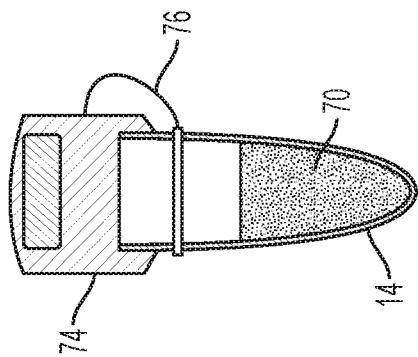
FIG. 25C is a perspective view of a container of a device for attached flow of blood, with the container removed from a housing in a second position, in accordance with an embodiment of the present invention.
Figure 25B:
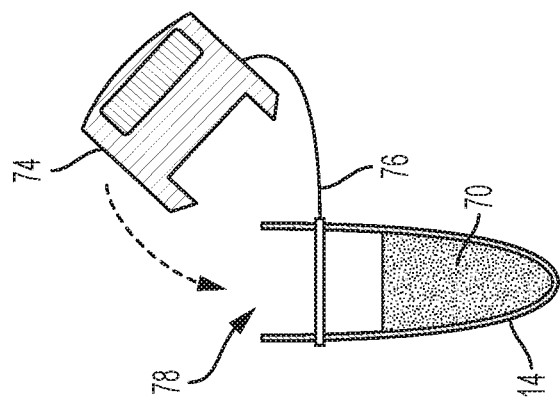
FIG. 25B is a perspective view of a container of a device for attached flow of blood, with the container removed from a housing in a first position, in accordance with an embodiment of the present invention.
Figure 25A:
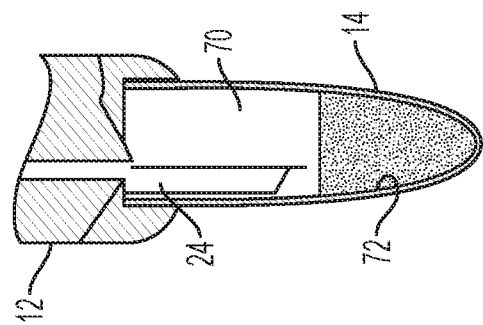
FIG. 25A is a perspective view of a container of a device for attached flow of blood, with the container connected to a housing, in accordance with an embodiment of the present invention.

Referring to FIGS. 25A-25C, in one embodiment, the container 14 includes a removably connectable cap 74 and a tether element 76. In such an embodiment, the cap 74 is removed when the container 14 is connected to the housing 12 as shown in FIG. 25A. The tether element 76 ensures that the cap 74 still remains secured to a portion of the container 14 with the cap 74 disconnected from an open top end 78 of the container 14 as shown in FIG. 25B. Once a desired amount of blood 16 is collected within the container 14, the container 14 is removed from the housing 12 and the cap 74 is connected to the container 14 to protectively seal the blood 16 within the container 14 as shown in FIG. 25C.

Figure 26A:
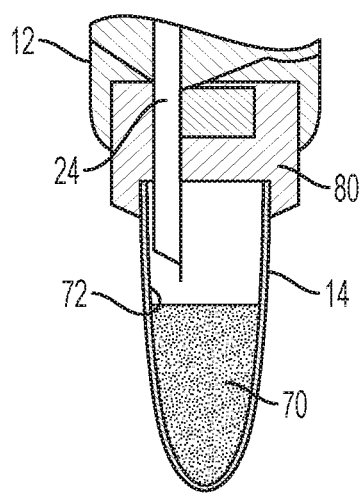
FIG. 26A is a perspective view of a container of a device for attached flow of blood, with the container connected to a housing, in accordance with another embodiment of the present invention.
Figure 26B:
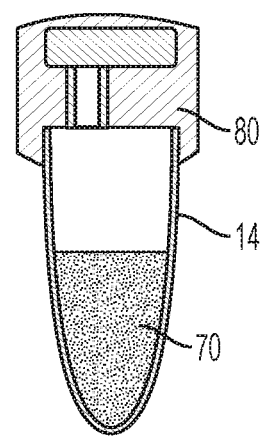
FIG. 26B is a perspective view of a container of a device for attached flow of blood, with the container removed from a housing, in accordance with another embodiment of the present invention.

Referring to FIGS. 26A-26B, in one embodiment, the container 14 includes a resealable septum 80. In such an embodiment, with the container 14 connected to the housing 12, a portion of the flow channel 24 pierces the septum 80 so that the flow channel 24 is in fluid communication with the collection cavity 70 of the container 14. Once a desired amount of blood 16 is collected within the container 14, the container 14 is removed from the housing 12 and the septum 80 automatically reseals to the closed, sealed position to protectively seal the blood 16 within the container 14 as shown in FIG. 26B.

Figure 27C:
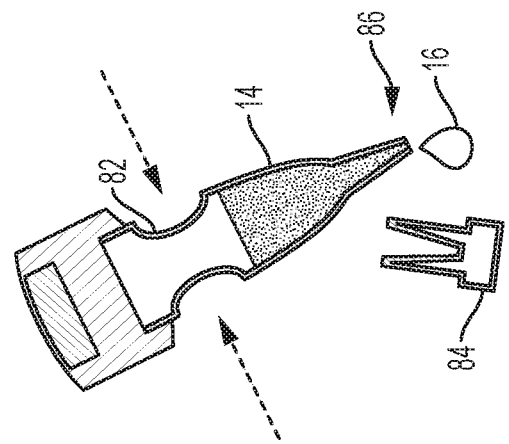
FIG. 27C is a perspective view of a container of a device for attached flow of blood, with the container removed from a housing in a second position, in accordance with another embodiment of the present invention.
Figure 27B:
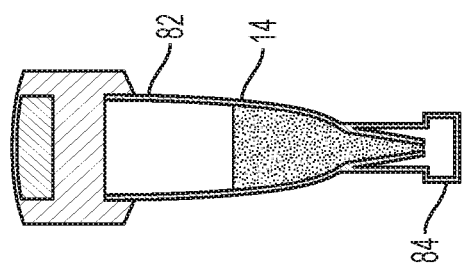
FIG. 27B is a perspective view of a container of a device for attached flow of blood, with the container removed from a housing in a first position, in accordance with another embodiment of the present invention.
Figure 27A:
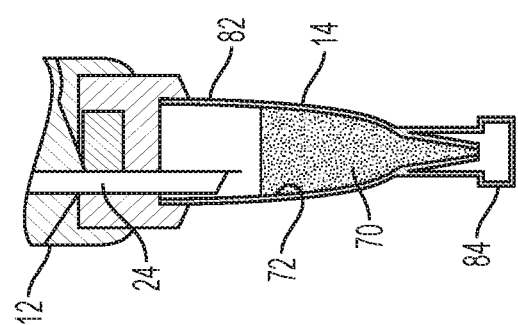
FIG. 27A is a perspective view of a container of a device for attached flow of blood, with the container connected to a housing, in accordance with another embodiment of the present invention.

Referring to FIGS. 27A-27C, in one embodiment, the container 14 includes a deformable dispensing portion 82. In such an embodiment, with the container 14 removed from the housing 12, a portion of the blood 16 may be dispensed from the container 14 by activation of the deformable portion 82. For example, the deformable portion 82 is transitionable between an initial position (FIGS. 27A-27B) in which the blood 16 is contained within the collection cavity 70 and a deformed position (FIG. 27C) in which a portion of the blood 16 is expelled from the collection cavity 70 of the container 14. The deformable portion 82 is squeezed to transition from the initial position (FIGS. 27A-27B) to the deformed position (FIG. 27C). In this manner, the blood 16 may be transferred to a device intended to analyze the sample, e.g., such as a point-of-care testing device, a cartridge tester, or a near patient testing device, while minimizing the exposure of the medical practitioner to the blood sample. In one embodiment, the container 14 also includes an end cap 84 to safely seal an exit portion 86 of the container 14. When a user is ready to expel a portion of blood 16 from the container 14, the end cap 84 is removed from the exit portion 86 of the container 14 before dispensing blood 16.

Figure 28A:
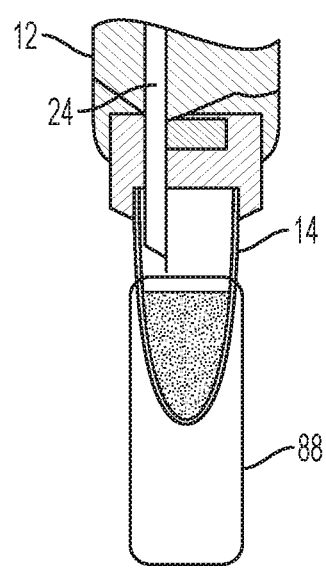
FIG. 28A is a perspective view of a container of a device for attached flow of blood, with the container connected to a housing, in accordance with another embodiment of the present invention.
Figure 28B:
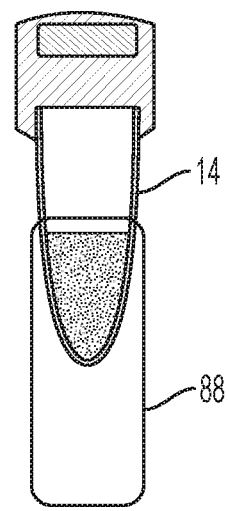
FIG. 28B is a perspective view of a container of a device for attached flow of blood, with the container removed from a housing in accordance with another embodiment of the present invention.

Referring to FIGS. 28A-28B, in one embodiment, the container 14 includes an extension tube 88. The extension tube 88 is compatible with analyzers and analyzing devices.

FIGS. 17-24 illustrate another exemplary embodiment of a device for attached flow of blood of the present disclosure. Referring to FIGS. 17-24, a device for attached flow of blood 100 of the present disclosure provides a controlled blood flow path that ensures attached blood flow from a collection site to a collection container.

Upon puncturing the skin of a patient using a lancet device, the blood will spread and remain on a surface of the finger. Without controlling the blood and the flow of blood, the blood will remain on a surface of the finger and will not flow to a collection container.

Referring to FIGS. 17-24, in one exemplary embodiment, a device for attached flow of blood 100 generally includes a housing 112 and a collection container 14 that is removably connectable to the housing 112. The container 14 defines a collection cavity 70 and includes an interior wall or interior wall surface 72. The same containers 14 that are compatible with the device 10 described above with reference to FIGS. 1-10B are compatible with the device 100 described with reference to FIGS. 17-24.

Figure 17:
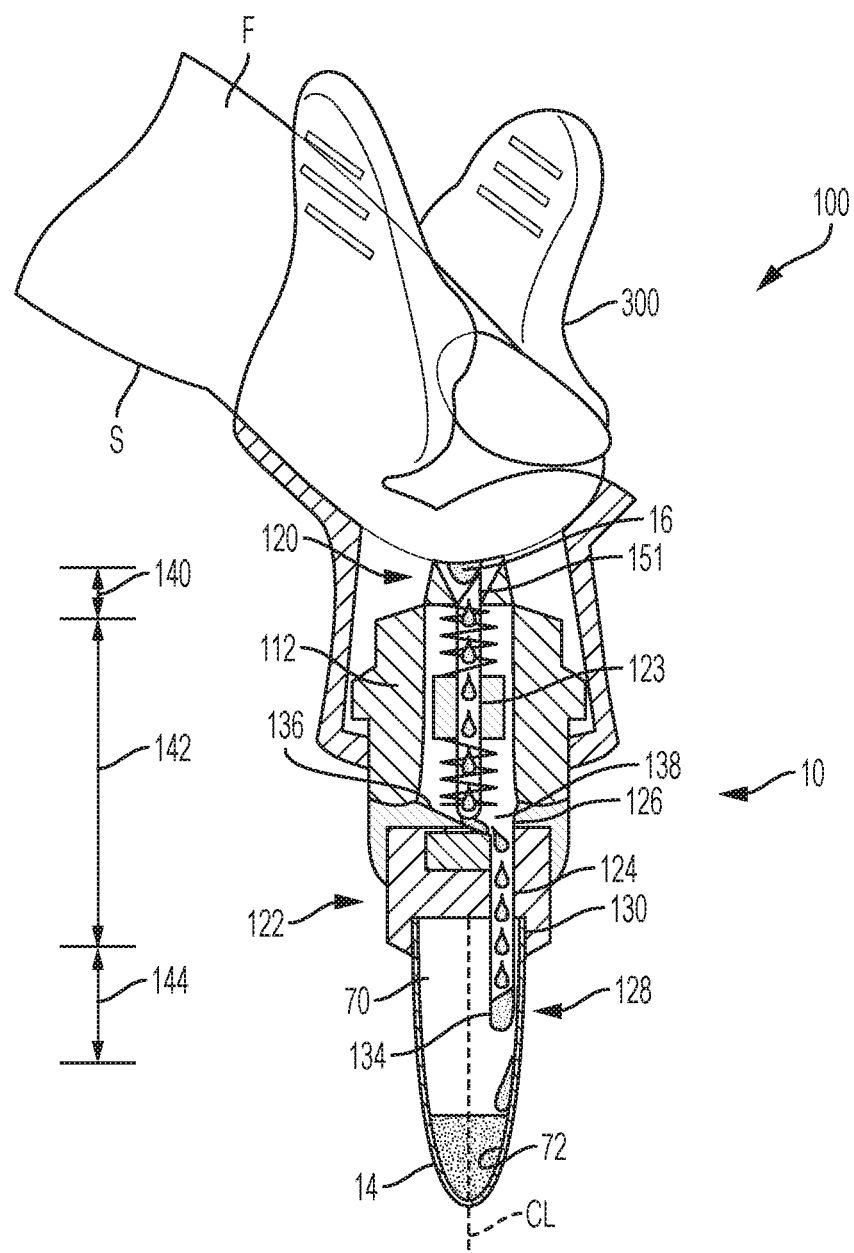
FIG. 17 is a cross-sectional view of a device for attached flow of blood engaged with a finger in accordance with another embodiment of the present invention.

Referring to FIG. 17, the housing 112 defines a centerline CL and includes a first end 120, a second end 122, a hollow needle 123, and a flow channel 124. The flow channel 24 includes an inlet 126 and an outlet 128. A portion of the flow channel 124, e.g., a bottom portion 130, is offset from the centerline CL of the housing 112. This ensures that the outlet 128 of the flow channel 124 is adjacent to an interior wall surface 72 of the container 14, as described in more detail below. The flow channel 124 also includes a flow directing attachment portion 134 at the outlet 128. In one embodiment, the outlet 128 of the flow channel 124 extends beyond the second end 122 of the housing 112 as shown in FIG. 17. In one embodiment, the hollow needle 123 is between the first end 120 of the housing 112 and the flow channel 124.

In the embodiment shown in FIGS. 17-24, the hollow needle 123 functions similar to the first flow directing attachment portion 32 described above with respect to device 10 shown in FIGS. 1-10B.

Referring to FIG. 17, with the container 14 connected to the housing 112, the outlet 128 of the flow channel 124 is in fluid communication with the collection cavity 70 of the container 14 and the outlet 128 of the flow channel 124 is adjacent the interior wall surface 72 of the container 14.

Upon puncturing the skin of a patient using a lancet device, the blood will spread and remain on a surface of the finger. Without controlling the blood and the flow of blood, the blood will remain on a surface of the finger and will not flow to a collection container.

The device for attached flow of blood 100 of the present disclosure provides a controlled blood flow path that ensures attached blood flow from a collection site to a collection container. The device for attached flow of blood 100 of the present disclosure achieves this using three key technical elements to control the flow of blood in the desired manner.

For example, referring to FIG. 17, with the first end 120 of the housing 112 in communication with a source of blood 16, the hollow needle 123, the flow channel 124, the flow directing attachment portion 134, and the interior wall surface 72 of the container 14 provide attachment portions to establish attached blood flow, for a first drop of blood 16 and subsequent blood 16 to follow, from the first end 120 of the housing 112 to the collection cavity 70 of the container 14.

The first key blood flow path element 140 involves directing the first drop of blood 16 away from the surface S of the finger F in a direction towards a collection container 14. In one embodiment, with the first end 120 of the housing 112 in communication with a source of blood 16, a first drop of blood 16 attaches to a portion of the hollow needle 123 and flows through the hollow needle 123 to the flow channel 124 in a controlled manner as shown in FIG. 17.

In this manner, a portion of the hollow needle 123 provides an attachment portion that functions similar to the first flow directing attachment portion 32 described above with respect to device 10 shown in FIGS. 1-10B. The device 100 of the present disclosure including a hollow needle 123 provides an advantage in that the hollow needle 123 can also be used to lance a skin surface S of a finger F to provide a source of blood 16. In such an embodiment, no separate lancet device is required. For example, in one embodiment, the hollow needle 123 may include a lancing blade 151 that can be used to lance a skin surface S of a finger F to provide a source of blood 16. In such an embodiment, with the first end 120 of the housing 112 in communication with a source of blood 16, a first drop of blood 16, and subsequent blood 16, attaches to the lancing blade 151 and flows through the hollow needle 123 to the flow channel 124.

After the first drop of blood 16 attaches to a portion of the hollow needle 123 and flows through the hollow needle 123, the subsequent blood 16 follows the attached blood flow path of the first drop of blood 16 from the first end 120 of the housing 112 to the collection cavity 70 of the container 14.

The second key blood flow path element 142 involves directing the blood 16 or pulling the blood 16 through the flow channel 124 to the flow directing attachment portion 134 via capillary motion. In one embodiment, the second key blood flow path element 142 involves directing the blood 16 or pulling the blood 16 through the hollow needle 123 and the flow channel 124 to the flow directing attachment portion 134 via capillary motion in a direction towards a collection container 14. For example, the first drop of blood 16, and subsequent blood 16, is pulled through the flow channel 124 to the flow directing attachment portion 134 via capillary motion. In one embodiment, the flow channel 124 is a capillary flow channel. In one embodiment, the flow channel 124 is a capillary tube that uses capillary forces to pull the blood 16 down the flow channel 124 away from the surface S of the finger F.

In one embodiment, the housing 112 includes a sloped wall surface 136 between the hollow needle 123 and the flow channel 124. In one embodiment, the sloped wall surface 138 defines a flow channel entry 138. In one embodiment, the sloped wall surface 136 provides a downward attached flow path from the hollow needle 123 to the flow channel 124 of the housing 112.

The third key blood flow path element 144 involves directing the blood 16 from the flow channel 124 into the collection container 14. The device 100 of the present disclosure ensures transition from the flow channel 124 to the container 14 via attached flow. For example, the blood 16 attaches to the flow directing attachment portion 134 and the interior wall surface 72 of the container 14 to flow from the flow channel 124 into the collection cavity 70 of the container 14.

The third key blood flow path element 144 involving directing the blood 16 from the flow channel 124 into the collection container 14 is the reason that it is important that a portion of the flow channel 124, e.g., a bottom portion 130, is offset from the centerline CL of the housing 112. This ensures that the outlet 128 of the flow channel 124, and the flow directing attachment portion 134, is adjacent to an interior wall surface 72 of the container 14 to ensure the transition of the attached blood flow from the flow channel 124 to the container 14.

The blood 16 will only flow down and out the flow channel 124 into the container 14 if the blood 16 is able to find another portion to attach to. The flow directing attachment portion 134 and the interior wall surface 72 of the container 14 provide such attachment portions to control the blood 16 to the collection cavity 70 of the container 14 via attached blood flow.

As described above, once this pathway of attached blood flow is established, the subsequent blood 16 follows and flows along this attached blood flow. In the above-described manner, the device 100 of the present disclosure establishes attached blood flow, for a first drop of blood 16 and subsequent blood 16 to follow, from the first end 120 of the housing 112 to a collection cavity 70 of the container 14.

As discussed above, a portion of the hollow needle 123 that provides an attachment portion for the flow of blood 16 functions similar to the first flow directing attachment portion 32 described above with respect to device 10 shown in FIGS. 1-10B.

The hollow needle 123 may include a variety of different designs and structures as shown in FIGS. 18-24. Additional alternative designs and structures of the hollow needle 123 are contemplated. For example, referring to FIGS. 18 and 19, in one embodiment, the hollow needle 123 includes a bevel cut hollow needle. In one configuration, the bevel of the needle may have a length of between 3 mm and 6 mm and the lumen inner diameter may be between 0.25 mm and 4 mm.

As discussed above, referring to FIGS. 20 and 21, in one embodiment, the hollow needle 123 may include a lancing blade 151 that can be used to lance a skin surface S of a finger F to provide a source of blood 16.

Referring to FIG. 21, in another embodiment, the hollow needle 123 includes a flow directing ring 155 around the hollow needle 123. The flow directing ring 155 prevents blood 16 from flowing down the hollow needle 123 and ensures that the blood 16 flows through the hollow needle 123 to the flow channel 124. FIGS. 22-24 illustrate additional alternative designs and structures of the hollow needle 123. The needle bevels serve as the additional first flow directed attachment sections, similar to the pillar structure portion 32 as described above with reference to FIG. 3.

The flow directing attachment portion 134 may include a variety of different designs and structures as shown in FIGS. 7A-10B. Additional alternative designs and structures of the flow directing attachment portion 134 are contemplated. The flow directing attachment portion 134 of device 100 may include the same designs and structures as the second flow directing attachment portion 34 of device 10 as described above and as shown in FIGS. 7A-10B.

Figure 11:
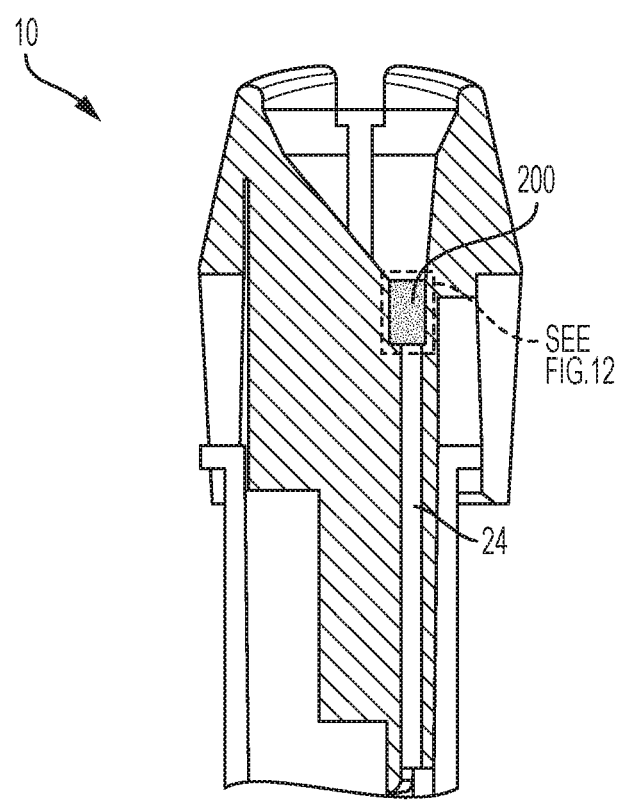
FIG. 11 is a cross-sectional view of a device for attached flow of blood in accordance with another embodiment of the present invention.
Figure 12:
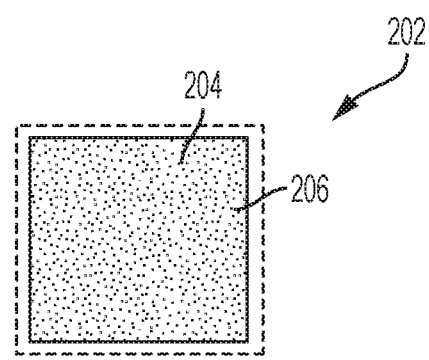
FIG. 12 is an enlarged view of an open cell foam material taken along section 12 of FIG. 11 in accordance with another embodiment of the present invention.

Another advantage of a device 10, 100 of the present disclosure is that the device 10, 100 is able to effectuate distributed mixing of a sample stabilizer 200 within a blood sample 16. Referring to FIGS. 11 and 12, in one embodiment, a sample stabilizer 200 is positioned within a portion of flow channel 24, 124 such that a blood sample 16, as the blood sample 16 follows the controlled attached blood flow from a collection site to a collection container of the present disclosure, will pass through the sample stabilizer 200. In this manner, the blood sample 16 may be mixed with a sample stabilizer 200, such as an anticoagulant or other additive, provided within a portion of device 10, 100. The sample stabilizer 200 can be an anticoagulant, or a substance designed to preserve a specific element within the blood such as, for example, RNA, protein analyte, or other element.

Referring to FIGS. 11 and 12, in one embodiment, the sample stabilizer 200 includes a material 202 including pores 204 and a dry anticoagulant powder 206 that is within the pores 204 of the material 202. In this manner, the device 10, 100 may include a dry anticoagulant, such as Heparin or EDTA, deposited on or within a portion of the flow channel 24, 124. In one embodiment, the material 202 is an open cell foam that contains dry anticoagulant dispersed within the cells of the open cell foam to promote the effectiveness of the flow-through mixing and anticoagulant uptake. In one embodiment, the sample stabilizer 200 is the dry anticoagulant powder 206.

In one embodiment, the open cell foam may be treated with an anticoagulant to form a dry anticoagulant powder 206 finely distributed throughout the pores 204 of the open cell foam. As the blood sample 16 flows through the flow channel 24, 124, the blood sample 16 passes through the open cell foam and is exposed to the anticoagulant powder 206 available throughout the internal pore structure of the open cell foam. In this manner, the blood sample 16 dissolves and mixes with the dry anticoagulant powder 206 while passing through the material 202 or open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

FIGS. 13-16 illustrate exemplary embodiments of a sample stabilizer 200 being including within a container 14.

Figure 13:
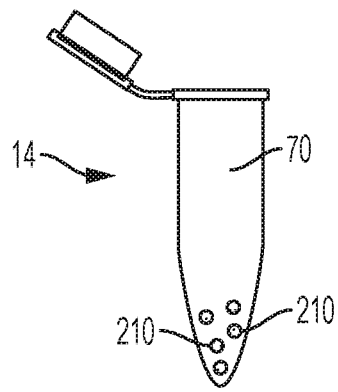
FIG. 13 is a perspective view of a container having a sample stabilizer in accordance with an embodiment of the present invention.

For example, referring to FIG. 13, in one embodiment, anticoagulant lyophilized spheres 210 are provided within collection cavity 70 of container 14. As blood 16 follows the attached flow of the present disclosure into the container 14, the anticoagulant lyophilized spheres 210 dissolve within the blood 16 upon contact with the blood 16.

Figure 14:
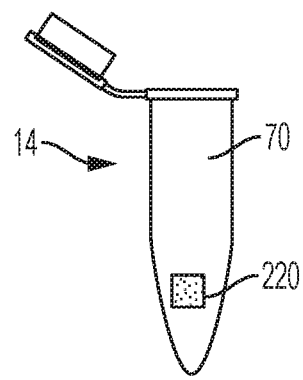
FIG. 14 is a perspective view of a container having a sample stabilizer in accordance with another embodiment of the present invention.
Figure 15:
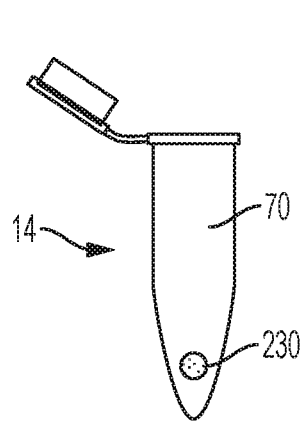
FIG. 15 is a perspective view of a container having a sample stabilizer in accordance with another embodiment of the present invention.
Figure 16:
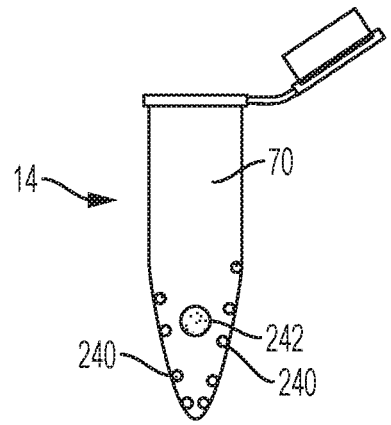
FIG. 16 is a perspective view of a container having a sample stabilizer in accordance with another embodiment of the present invention.

Referring to FIG. 14, in another embodiment, the sample stabilizer 200 includes a floating anticoagulant coated open cell foam material 220. Referring to FIG. 15, in another embodiment, the sample stabilizer 200 includes a floating anticoagulant coated floating ball 230. Referring to FIG. 16, in another embodiment, the container 14 includes an anticoagulant coated wall surface 240 and a mixing ball 242.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A device for attached flow of blood, the device comprising:
    a housing defining a centerline and having a first end, a second end, and a flow channel having an inlet and an outlet, a portion of the flow channel offset from the centerline of the housing, and the flow channel having a first flow directing attachment portion adjacent to the inlet and a second flow directing attachment portion adjacent to the outlet, the first flow directing attachment portion provides a first fluid attachment point for controlling the flow of blood that attaches thereto from a skin surface to a portion of the housing; and a container removably connectable to the housing, the container having an interior wall defining a collection cavity, wherein, with the container connected to the housing, the outlet of the flow channel is in fluid communication with the collection cavity of the container and the outlet of the flow channel is adjacent to the interior wall of the container, the outlet of the flow channel and the second flow directing attachment portion are configured to provide a second fluid attachment point for attached flow of blood directly from the flow channel to the interior wall of the container, wherein the first end of the housing includes a sloped wall surface, and wherein the first flow directing attachment portion is an attachment pillar and extends entirely from the sloped wall surface along the centerline.

2. The device of claim 1, wherein, with the first end of the housing in communication with a source of blood, the first flow directing attachment portion, the flow channel, the second flow directing attachment portion, and the interior wall of the container provide attachment portions to establish attached blood flow, for a first drop of blood and subsequent blood to follow, from the first end of the housing to the collection cavity of the container.

3. The device of claim 1, wherein, with the inlet of the flow channel in communication with a source of blood, the blood fluidly attaches to the first flow directing attachment portion and flows from the first flow directing attachment portion to the flow channel.

4. The device of claim 3, wherein the blood is subsequently pulled through the flow channel to the second flow directing attachment portion via capillary action.

5. The device of claim 4, wherein, the blood fluidly attaches to the second flow directing attachment portion and the interior wall of the container to flow from the flow channel into the collection cavity of the container.

6. The device of claim 1, wherein the sloped wall surface defines a flow channel entry.

7. The device of claim 1, wherein the first flow directing attachment portion comprises a plurality of attachment pillars.

8. The device of claim 1, wherein the second flow directing attachment portion is an attachment lip.

9. The device of claim 1, wherein the second flow directing attachment portion is an extended capillary tube portion.

10. The device of claim 1, wherein the second flow directing attachment portion is an inward curved lip.

11. The device of claim 1, wherein the second flow directing attachment portion is a planar cut lip.

12. The device of claim 1, wherein the second flow directing attachment portion is an extended pillar structure.

13. The device of claim 1, wherein the outlet of the flow channel extends beyond the second end of the housing.

14. The device of claim 1, wherein the attachment pillar is cylindrical.

15. The device of claim 14, wherein the attachment pillar comprises hydrophilic surface properties.

16. The device of claim 14, wherein the attachment pillar has a diameter of between 0.25 mm to 4 mm.

17. The device of claim 16, wherein the attachment pillar has a length of between 2 mm and 20 mm.

18. The device of claim 1, wherein a center of the outlet of the flow channel is closer to the interior wall of the container than to the centerline of the housing.

* * * * *